United States Patent [19]

Suzukamo et al.

[11] Patent Number: 4,954,651
[45] Date of Patent: Sep. 4, 1990

[54] PROCESS FOR PREPARING TRANS-2,2-DIMETHYL-3-(2,2-DIHALOVINYL)-CYCLOPROPANE CARBOXYLIC ACID HALIDE

[75] Inventors: Gohfu Suzukamo, Osaka, Japan; Yoji Sakito, Montreal, Canada; Masami Fukao, Shiga; Koji Hagiya, Osaka, both of Japan

[73] Assignee: Sumitomo Chemical Company, Limited, Osaka, Japan

[21] Appl. No.: 345,726

[22] Filed: May 1, 1989

[30] Foreign Application Priority Data

May 2, 1988 [JP] Japan .................................. 63-109456
May 26, 1988 [JP] Japan .................................. 63-128625

[51] Int. Cl.$^5$ .................................................. C07C 5/00
[52] U.S. Cl. ...................................... 562/856; 562/849
[58] Field of Search .................. 562/866, 867, 856, 849

[56] References Cited

U.S. PATENT DOCUMENTS 3,578,688  5/1971  Fenton .............................. 260/405.6
4,485,257  11/1984  Suzukamo et al. ................. 562/887

FOREIGN PATENT DOCUMENTS 50-160242  6/1974  Japan .
50-131953  10/1975  Japan .
63-275543  11/1988  Japan .
1446304  8/1976  United Kingdom .

OTHER PUBLICATIONS

The Japan Chemical Society, 56th Spring Annual Meeting, 1988, p. 1833.

*Primary Examiner*—Michael L. Shippen
*Attorney, Agent, or Firm*—Birch, Stewart, Kolasch & Birch

[57] ABSTRACT

Trans-2,2-dimethyl-3-(2,2-dihalovinyl)-cyclopropane carboxylic acid halides which are an intermediate for insecticides are prepared by allowing arylphosphines to react with cis- or cis-/trans-mixed 2,2-dimethyl-3-(2,2-dihalovinyl)-cyclopropane carboxylic acid halides of the formula

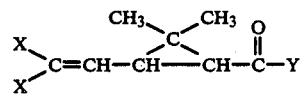

wherein both X and Y are halogen atoms, respectively, at a temperature of −10° to 100° C., in the presence of absence of halogen compounds.

29 Claims, No Drawings

PROCESS FOR PREPARING TRANS-2,2-DIMETHYL-3-(2,2-DIHALOVINYL)-CYCLOPROPANE CARBOXYLIC ACID HALIDE

The present invention relates to a process for preparing trans-2,2-dimethyl-3-(2,2-dihalovinyl)-cyclopropane carboxylic acid halide having the formula

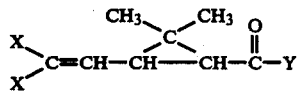

wherein X and Y stand for halogen atoms, respectively.

2,2-Dimethyl-3-(2,2-dihalovinyl)-cyclopropan carboxylic acid (hereinafter referred to as dihalo acid) is an acid moiety of permethrin, cypermethrin, etc., that are low mammalian toxic insecticides which are familier as household ones and are strongly active against pests of agricultural crops or forest insects. Dihalo acid halides are useful for intermediates of these insecticides.

Dihalo acid halides have, .geometrical isomers, cis and trans, based on the cyclopropane ring. It has been known that, in general, among the isomers, the esters derived from trans-isomers are less toxic against mammals than those derived from cis-isomers (Nature 244, 456, 1973). Dihalo acids when industrially produced are a mixture of trans- and cisisomers. Accordingly, it is a problem to convert cis-isomers to trans-isomers, particluarly on a commerical scale. One of the processes for the conversion is heating dihalo acid halides at a temperature not lower than 160 ° C. (Japanese Kokai 50-131953). This process needs higher temperature, but conversion to trans-isomers rarely proceeds at a temperature, for example, 80 ° C.

After an extensive study, the present inventors succeeded in finding the fact that such bases as arylphosphines, pyridines etc. effect the conversion under mild conditions and that the presence of halides facilitates to allow the conversion to proceed more smoothly. The present invention has been established on the basis of such finding and additional research.

According to the present invention, economical processes are provided, i.e., a process where bases selected from arylphosphines and pyridines are allowed to react with cis- or cis/trans-mixed dihalo acid halides of the formula

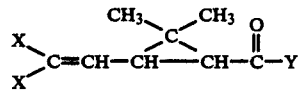

wherein both X and Y stand for halogen atoms, until trans2,2-dimethyl-3-(2,2-dihalovinyl)-cyclopropane carboxylic acid halides are produced and a process where the reaction above is allowed to proceed in the presence of halogen compounds until trans-dihalo acid halides are produced.

Dihalo acid halides, the starting compound in the present process, include, for example, those wherein a substituent X is a halogen atom such as fluorine, chlorine or bromine and a substituent Y is a halogen atom such as chlorine or bromine. They are, for example, dichloro acid chloride, difluoro acid chloride, chlorofluoro acid chloride, dichloro acid bromide, dibromo acid chloride or dibromo acid bromide. Usually,, dihalo acid chlorides are preferable from the point of convenience in handling and cost.

Dihalo acid halides may be in the form of cis-isomers alone or any mixtures with trans-isomers. Preferable are cis-isomers alone or mixtures rich in cis-isomers.

Arylphosphines include triarylphosphines such as triphenylphosphine, tri(o-tolyl)phosphine, tri(m-tolyl)-phosphine, tri(p-tolyl)phosphine, tri(chlorophenyl)-phosphine or tri(bromophenyl)phosphine, tetraphenyl diphosphine, halodiarylphosphines such as chlorodiphenylphosphine, bromodiphenylphosphine, chlorodi(-tolyl)phosphine, chlorodi(chlorophenyl)phosphine or chlorodi(bromophenyl)phosphine and dihaloarylphosphine such as dichlorophenylphosphine or dibromophenylphosphine. Preferable are triarylphosphines. They are used in an amount of, usually, 1/200–1 times, preferably, 1/100–½ times as much dihalo acid halides, in moles.

The conversion reaction to trans-isomers proceeds with arylphosphines alone, but is facilitated in the presence of halogen compounds. The halogen compounds are alkaline earth metal halides such as magnesium iodide, magnesium bromide, magnesium chloride, calcium iodide or calcium bromide; quaternary phosphonium halides such as tetraphenyl phosphonium iodide, bromide or chloride, tetramethyl phosphonium iodide, bromide or chloride, tetrapropyl phosphonium iodide, bromide or chloride, tetrabutyl phosphonium iodide, bromide or chloride or methyltriphenyl phosphonium iodide, bromide or chloride; iodine; bromine; halides of iodine or bromine such as iodine monobromide, iodine monochloride, iodine trichloride or bromine monochloride; quaternary ammonium iodide or bromide such as tetramethylammonium iodide or bromide, tetraethylammonium iodide or bromide, tetrapropylammonium iodide or bromide, tetrabutylammonium iodide or bromide, cetyltrimethylammonium iodide or bromide, trimethylbenzylammonium iodide or bromide, triethylbenzylammonium iodide or bromide; iodides or bromides of alkali metals such as lithium iodide or bromide, sodium iodide or bromide, potassium iodide or bromide, cesium iodide or bromide; iodides or bromides of phosphorus such as phosphorus iodide or phosphorus pentabromide, phosphorus tribromide; alkyl or aralkyl iodide such as iodomethane, iodoethane, 1-iodopropane, 2-iodopropane, 1-iodobutane, 2-iodobutane, 1-iodo-2-methylpropane, 2-iodo-2-methylpropane, iodopentane, iodohexane, iodooctadecane, benzyl iodide; iodide or bromide of hydrogen such as hydrogen iodide or hydrogen bromide Preferable are iodine compounds. Halogen compounds are used in an amount of usually 1/100–2 times, preferably, 1/50–½ times as much arylphosphines, in moles.

The conversion reaction is conducted usually in the presence of an inert organic solvent. Examples on inert organic solvents are halogenated hydrocarbons such as methylene dichloride, chloroform, carbon tetrachloride, dichloroethane, chlorobenzene or o-dichlorobenzene; nitriles such as acetonitrile, propionitrile or butyronitrile; aprotic polar solvent such as dimethyl formamide, dimethyl sulfoxide; ketones such as acetone, methylethyl ketone or methylisobutyl ketone or esters such as methyl acetate, ethyl acetate or butyl acetate. Preferable are halogenated hydrocarbons and nitriles.

The conversion reaction is conducted in such a manner that arylphosphines are added to a solution of dihalo acid halides in solvents. When halogen compounds are used, they are added thereto.

The conversion is effected usually at a temperature of from −10 to 100° C., preferably 0–80° C., although the temperature varies depending on the amounts and kinds of arylphosphines or halogen compounds employed.

Reaction time is usually from 10 min. to 20 hours, although it varies depending on the amounts and kinds of arylphosphines or halogen compounds employed, too.

Progress of the reaction can be determined by sampling a portion of reaction mixture and analysis by gas chromatography or NMR spectra.

When pyridines are used, they may be pyridine; picolines such as 2-picoline, 3-picoline, 4-picoline; ethyl pyridines such as 2-ethylpyridine, 3-ethylpyridine, 4-ethylpyridine; lutidines such as 2,3-lutidine, 2,4-lutidine, 2,5-lutidine, 2,6-lutidine, 3,4-lutidine, 3,5-lutidine; propylpyridines such as 2-propylpyridine, 3-propylpyridine, 4-propylpyridine; benzylpyridines such as 2-benzylpyridine, 3-benzylpyridine, 4-benzylpyridine; arylpyridines such as 2-phenylpyridine, 3-phenylpyridine, 4-phenylpyridine, 4,4'-dipyridyl, 2,2'-dipyridyl, 3,3'-dipyridyl; quinoline, isoquinoline. Preferable are pyridine, picolines, lutidines and isoquinoline.

They are used in an amount usually of 1/100–5 times, preferably, ¼–1 times as much dihalo acid halides, in moles.

Halogen compounds used together with pyridine are, for example, halides of iodine such as iodine, iodine monobromide, iodine monochloride, iodine trichloride; iodides of alkali metals such as lithium iodide, sodium iodide, potassium iodide, cesium iodide; iodine substituted hydrocarbons of $C_1$–$C_{18}$ such as iodomethane, iodoethane, 1-iodopropane, 2-iodopropane, 1-iodobutane, 2-iodobutane, 1-iodo-2-methylpropane, 2-iodo-2-methylpropane, iodopentane, iodohexane, iodoheptane, iodooctane, iodooctadecane, benzyl iodide; iodides of quaternary amines having hydrocarbon chains of $C_3$–$C_{16}$ such as tetramethylammonium iodide, tetraethylammonium iodide, tetrapropylammonium iodide, tetrabutylammonium iodide, trimethylbenzylammonium iodide, triethylbenzylammonium iodide; iodides of quaternary phosphorus compounds having hydrocarbon chains of $C_3$–$C_{24}$ such as tetraphenylphosphonium iodide; tetramethylphosphonium iodide, tetraethylphosphonium iodide, tetrapropylphosphonium iodide, tetrabutylphosphonium iodide, methyltriphenylphosphonium iodide; iodine compounds such as hydrogen iodide. They are used in an amount of usually 1/50 –1 times, preferably 1/20 –¼ times as much dihalo acid halides, in moles.

Reaction is usually conducted in the presence of an inert solvent. The same solvents as those used for arylphosphines may be employed, but preferable is acetonitrile. Alternatively, pyridine may be employed.

Reaction is carried out in such a manner that pyridine and halogen compounds are added to a solution of dichloro acid halides in solvents.

Reaction temperature is usually 10–150° C., preferably 60–120° C., although it varies depending on amounts and varieties of pyridines and halogen compounds.

Reaction time is usually 1–15 hours, although it varies depending on amounts and varieties of pyridines and halogen compounds, too.

Progress of the reaction can be determined by sampling a portion of reaction mixture and analysis by means of gas chromatography or NMR spectra.

Trans dihalo acid halides thus produced may be isolated by removing catalysts from a reaction mass and then if necessary, distilling the residual solution. Alternatively, the isolation may not be effected. The trans dihalo acid halide can be directly subjected to the reaction with an alcohol which is 3-phenoxybenzyl alcohol, 5-benzyl-3-furylmethyl alcohol, 4-methyl-3-hepten-t-in-5-ol, 4-fluoro-3-hepten-6-in-5-ol or the like in the presence of hydrogen halide eliminating agent to obtain low mammalian toxic insecticides.

Alcohols such as methanol or ethanol may be added to the reaction mass until direct esterification is effected. The product obtained may be subjected to biochemically optical resolution. Alternatively, for instance, alkaline aqueous solution is added to the product above to effect hydrolysis and neutralized with a mineral acid, whereby the corresponding free acid can be obtained.

According to the present invention, trans-dihalo acid halides are obtained under milder conditions than the conventional processes.

The present invention is further explained in more detail by the following examples.

EXAMPLE 1

Triphenylphosphine (231 mg) and iodine (112 mg) were added under a nitrogen atmosphere to a solution of dichloro acid chloride (1 g; cis 45 %, trans 55 %) in 1,2-dichloroethane (6.3 g) and the mixture was stirred at 25° C. for three hours.

After the reaction, 15 % aqueous sodium hydroxide solution was added to effect hydrolysis. The hydrolyzed product was acidified with 70% $H_2SO_4$ and extracted with toluene. Toluene was distilled off to obtain a white solid (870 mg) which was identified as dichloro acid by by an IR spectrum measurement.

A part of the solid taken as a sample was converted to the ethyl ester thereof by a usual manner. Gas chromatographic analysis gave the following results: cis 14.7 % trans 85.3%.

EXAMPLE 2

Triphenylphosphine (122 mg) and tetraphenylphosphonium iodide (102 mg) were added under a nitrogen atmosphere to a solution of the same dichloro acid chloride (1.05 g) as used in Example 1 in 1,2-dichloroethane (6.3 g). The mixture was stirred at 25° C. for three hours.

After the reaction, the similar procedure to that in Example 1 was applied to obtain dichloro acid (680 mg).

Isomer ratio: cis 15.3 % trans 84.7 %.

EXAMPLE 3

Example 2 was repeated except that the reaction was carried out at 0° C. for five hours in place of 25° C. for three hours.

Isomer ratio: cis 12.9 % trans 87.1 %.

EXAMPLE 4

Chlorodiphenylphosphine (340 mg) and iodine (440 mg) were added under a nitrogen atmosphere to a solution of dichloro acid chloride (1.54 g; cis 96.3 %, trans 3.7 %) in chlorobenzene (22 g). The mixture was stirred at 100° C. for three hours.

After the reaction, the mixture was cooled down to room temperature. Ethanol (380 mg) and pyridine (640 mg) were added thereto and the mixture was stirred at room temperature for one hour, washed with water and subjected to distillation to remove the solvent. The residue was distilled to obtain a fraction (1.52 g, a boiling point: 88–90° C. /1 mm Hg).

This product was confirmed to be dichloro acid ethyl ester by IR spectrum. Gas chromatographic analysis gave the following results: cis 28.2 % and trans 71.8 %.

EXAMPLE 5

Triphenylphosphine (230 mg) and phosphorus pentabromide (380 mg) were added under a nitrogen atmosphere to a solution of the same dichloro acid chloride (1.57 g) as used in Example 1 in chlorobenzene (22 g) and the mixture was stirred at 80° C. for 6 hours.

After the reaction, the similar procedure to that in Example 4 was applied to obtain dichloro acid ethyl ester. Isomer ratio: cis 38.7 %, trans 61.3 %.

EXAMPLE 6

Example 5 was repeated except that triphenylphosphine (843 mg) and phosphorus tribromide (855 mg) were used in place of the triphenylphosphine (230 mg) and phosphorus pentabromide, and the mixture was stirred for 3 hours at 100° C. in place of 80° C. for 6 hours.

Isomer ratio: cis 19.4 %, trans 80.6 %.

EXAMPLE 7

Example 4 was repeated except that acetonitrile (15 g), triphenylphosphine (360 mg) and sodium iodide (207 mg) were used in place of the chlorobenzene, chlorodiphenylphosphine and iodine, respectively, and the mixture was stirred at 25° C. for 2 hours, in place of 100° C. for 3 hours, thereby to obtain dichloro acid ethyl ester (1.5 g).

Isomer ratio: cis 14.5 %, trans 85.5 %.

EXAMPLE 8

Example 4 was repeated except that 1,2-dichloroethane (7.4 g), tri-p-tolylphosphine (414 mg) and iodine (178 mg) were used in place of the chlorobenzene, chlorodiphenylphosphine and iodine (440 mg), respectively, and the mixture was stirred at 25° C. for 3 hours, in place of 100° C. for 3 hours, thereby to obtain dichloro acid ethyl ester (1.52 g). Isomer ratio: cis, 15.4 %, trans, 84.6 %.

EXAMPLE 9

Example 4 was repeated except that 1,2-dichloroethane (4.56 g), tetraphenyldiphosphine (501 mg) and iodine (173 mg) were used in place of the chlorobenzene, chlorodiphenylphosphine and iodine (440 mg), respectively, and the mixture was stirred at 80° C. for 3 hours, in place of 100° C. for 3 hours, thereby to obtain dichloro acid ethyl ester (1.51 g). Isomer ratio: cis, 38 %, trans, 62 %.

EXAMPLE 10

Example 4 was repeated except that chlorobenzene (10.8 g), dichlorophenylphosphine (370 mg) and iodine (524 mg) were used in place of the chlorobenzene (22 g), chlorodiphenylphosphine and iodine (440 mg), thereby to obtain dichloro acid ethyl ester (1.49 g). Isomer ratio: cis, 26.5 %, trans, 73.5 %.

EXAMPLE 11

Example 4 was repeated except that 1,2-dichloroethane (22 g), triphenylphosphine (364 mg) and tetraphenylphosphonium bromide (583 mg) were used in place of the chlorobenzene, chlorodiphenylphosphine and iodine, respectively and the mixture was stirred at 80° C. for 7 hours in palce of 100° C. for 3 hours, thereby to obtain dichloro acid ethyl ester (1.44 g).

Isomer ratio: cis, 25.6 %, trans, 74.4 %.

EXAMPLE 12

Example 4 was repeated except that triphenylphosphine (509 mg) and cetyltrimethyl ammonium bromide (71 mg) were used in place of the chlorodiphenylphosphine and iodine, respectively, and the mixture was stirred at 80° C. for 8 hours in place of 100° C. for 3 hours, thereby to obtain dichloro acid ethyl ester (1.5 g).

Isomer ratio: cis, 43.7 %, trans, 56.3 %.

EXAMPLE 13

Example 4 was repeated except that acetonitrile (13 g), triphenylphosphine (314 mg) and magnesium chloride (118 mg) were used in place of the chlorobenzene, chlorodiphenylphosphine and iodine and the mixture was stirred at 80° C. for 2 hours in palce of 100° C. for 3 hours.

Isomer ratio: cis, 17.4 %, trans, 82.6 %.

EXAMPLE 14

Example 13 was repeated except that triphenylphosphine (385 mg) was used without the mangesium chloride and the mixture was stirred at 80° C. for 3 hours in place of 80° C. for 2 hours.

Isomer ratio: cis, 49.2 %, trans, 50.8 %.

EXAMPLE 15

Example 4 was repeated except that 1,2-dichloroethane (25 g), triphenylphosphine (392 mg) and solution (2.06 g) of HBr (5.7 wt%) in dichloroethane were used in place of the chlorobenzene, chlorodiphenylphosphine and iodine, respectively, and the mixture was stirred at 80° C. for 2.5 hours in place of 100° C. for 3 hours.

Isomer ratio: cis, 16.9 %, trans, 83.1 %.

EXAMPLE 16

Example 4 was repeated except that acetonitrile (16 g), triphenylphosphine (373 mg) and methyl iodide (308 mg) were used in place of the chlorobenzene, chlorodiphenylphosphine and iodine, respectively, and the mixture was stirred at 25° C. for 2 hours in place of 100° C. for 3 hours.

Isomer ratio: cis, 13 %, trans, 87 %.

COMPARATIVE EXAMPLE 1

Example 4 was repeated except that no chlorodiphenylphosphine and no iodine were used and the mixture was stirred at 100° C. for 8 hours, in place of 100° C. for 3 hours.

Isomer ratio: cis, 94.7 %, trans, 5.3 %.

EXAMPLE 17

Pyridine (348 mg) and iodine (223 mg) were added under a nitrogen atmosphere to a solution of dichloro acid chloride (cis, 96.8 %, trans, 3.2 %) in acetonitrile (20 g) and the mixture was stirred at 80° C. for 3 hours.

After the reaction, the mixture was cooled down to room temperature. To the soltuion were added ethanol (485 mg) and pyridine (834 mg) and the mixture was stirred at room temperature for one hour. The mixture was washed with water and distilled off the solvent.

The residue was distilled to obtain a fraction (2.01 g; a boiling point: 88–90° C./1 mmHg). The fraction was identified as dichloro acid ethyl ester by IR spectrum.

Gas chromatographic analysis gave the following isomer ratio: cis, 18.0 %, trans, 82.0 %.

EXAMPLE 18

3-Picoline (409 mg) and iodine (223 mg) were added under a nitrogen atmosphere to a solution of the same dichloro acid chloride (2 g) as used in Example 17 in acetonitrile (10 g). The mixture was stirred at 80° C. for 8 hours.

After the reaction, the similar procedure to that in Example 17 was applied to obtain dichloro acid ethyl ester (1.90 g). Gas chromatographic analysis gave the following isomer ratio: cis, 16.0 %, trans, 84.0 %.

EXAMPLE 19

Isoquinoline (568 mg) and iodine (223 mg) were added under a nitrogen atmosphere to a solution of the same dichloro acid chloride (2 g) as used in Example 17 in acetonitrile (10 g). The mixture was stirred at 80° C. for 6 hours.

After the reaction, the similar procedure to that in Example 17 was applied to obtain dichloro acid ethyl ester. The isomer ratio: cis, 21.2 %, trans, 78.8 %.

EXAMPLE 20

Pyridine (348 mg) and iodine bromide (182 mg) were added under a nitrogen atmosphere to a solution of the same dichloro acid chloride (2 g) as used in Example 17 in acetonitrile (10 g). The mixture was stirred at 80° C. for 6 hours.

After the reaction, the similar procedure to that in Example 17 was applied to obtain dichloro acid ester (2.06 g). Isomer ratio: cis, 33.4 %, trans, 66.6 %.

EXAMPLE 21

Pyridine (348 mg) and methyl iodide (176 mg) were added under a nitrogen atmosphere to a solution of the same dichloro acid chloride (2 g) as used in Example 17 in acetonitrile (10 g). The mixture was stirred at room temperature for 5 hours.

After the reaction, the similar procedure to that in Example 17 was applied to obtain dichloro acid ethyl ester (1.99 g). Isomer ratio: cis, 40.5 %, trans, 59.5 %.

EXAMPLE 22

3-Picoline (409 mg) and iodine (223 mg) were added under a nitrogen atmosphere to a solution of dichloro acid chloride (2 g, cis, 96.3 %, trans, 3.7 %) in dichloroethane (10 g). The mixture was stirred at 80° C. for 6 hours.

After the reaction, the similar procedure to that in Example 17 was applied to. Gas chromatographic analysis of the product obtained gave the following isomer ratio: cis, 22.4 %, trans, 77.6 %.

EXAMPLE 23

Pyridine (174 mg) and iodine (111 mg) were added under a nitrogen atmosphere to a solution of dichloro acid chloride (1.0 g, cis, 45.0 %, trans, 55.0 %) in 1,2-dichloroethane (6.3 g). The mixture was stirred at 80° C. for 3 hours.

After the reaction, the mixture was cooled down to room temperature, hydrolyzed with 15 % sodium hydroxide solution, acidified with 70 % sulfuric acid and extracted with toluene. Toluene was distilled off to obtain a white solid (893 mg) which was identified as dichloro acid by IR spectrum.

A part of the solid taken as a sample was converted to ethyl ester thereof by a usual manner. Gas chromatographic analysis gave the following results: cis, 22.9 %, trans, 77.1 %.

EXAMPLE 24

Pyridine (364 mg) and tetrabutyl ammonium iodide (332 mg) were added under a nitrogen atmosphere to a solution of the same dichloro acid chloride (2 g) as used in Example 17 in acetonitrile (10.0 g). The mixture was stirred at 80° C. for 3 hours. After the reaction, the similar procedure to that in Example 17 was applied to. Gas chromatographic analysis of the product thus obtained gave the following isomer ratio: cis, 17.7 %, trans, 82.3 %.

EXAMPLE 25

Pyridine (362 mg) and tetraphenylphosphonium iodide (411 mg) were added under a nitrogen atmosphere to a solution of the same dichloro acid chloride (2.0 g) as used in Example 17 in acetonitrile (10 g). The mixture was stirred at 80° C. for 6 hours. Then, the similar procedure to that in Example 17 was applied to. Gas chromatographic analysis of the product obtained gave the following isomer ratio: cis, 15.1 %, trans, 84.9 %.

EXAMPLE 26

Pyridine (355 mg) and solution (1.79 g) of hydrogen iodide (6.3 wt%) in dichloroethane were added under a nitrogen atmosphere to a solution of the same dichloro acid chloride (2 g) as used in Example 17 in 1,2-dichloroethane (10.0 g). The mixture was stirred at 80° C. for 6 hours.

Then, the similar procedure to that in Example 17 was applied to. Gas chromatographic analysis of the product thus obtained gave the following isomer ratio: cis, 31.6 %, trans, 68.4 %.

EXAMPLE 27

Pyridine (348 mg) and sodium iodide (661 mg) were added under a nitrogen atmosphere to a solution of the same dichloro acid chloride (1.0 g) as used in Example 22 in acetonitrile (11 g). The mixture was stirred at 80° C. for 2 hours.

Then, the similar procedure to that in Example 17 was carried out to obtain dichloro acid ethyl ester (981 mg). The isomer ratio: cis, 12.4 %, trans, 87.6 %.

EXAMPLE 28

4,4'-Dipyridyl (687 mg) and iodine (224 mg) were added under a nitrogen atmosphere to a solution of the same dichloro acid chloride (2.0 g) as used in Example 17 in acetonitrile (10 g). The mixture was stirred at 80° C. for 6 hours.

After the reaction, the similar procedure to that in Example 17 was applied to. Gas chromatographic analysis of the product gave the results: cis, 44.6 %, trans, 55.4 %.

COMPARATIVE EXAMPLE 2

Pyridine (353 mg) was added under a nitrogen atmosphere to a solution of the same dichloro acid chloride (2.0 g) as used in Example 17 in acetonitrile (20 g). The mixture was stirred at 80° C. for 8 hours.

Then, the product was converted to ethyl ester. Gas chromatographic analysis gave the following results: cis, 70 %, trans, 30 %.

COMPARATIVE EXAMPLE 3

A solution of the same dichloro acid chloride (2.0 g) as used in Example 17 in acetonitrile (20 g) was heated under a nitrogen atmosphere at 80° C. for 8 hours.

Then, the product was converted to ethyl ester. Gas chromatographic analysis gave the results: cis, 94.2 %, trans, 5.8 %.

We claim:

1. A process for preparing trans-2,2-dimethyl-3(2,2-dihalovinyl)-cyclopropane carboxylic acid halides which comprises reacting arylphosphine with cis- or a cis/trans-mixture of 2,2dimethyl-3-(2,2-dihalovinyl)-cyclopropane carboxylic acid halide of the formula $$\begin{array}{c} CH_3 \quad CH_3 \quad O \\ X \quad \diagdown C \diagup \quad \parallel \\ \diagdown C=CH-CH-CH-C-Y \\ X \diagup \end{array}$$

wherein both X and Y are halogen atoms, respectively, in the presence or absence of an inert solvent and in the presence or absence of a halogen compound.

2. A process according to claim 1, wherein the arylphosphine is used in an amount of 1/200 -1 times as much acid halide, in moles.

3. A process according to claim 1, wherein the arylphosphine is selected from the group consisting of triarylphosphines, tetraaryldiphosphines, halodiarylphosphines and dihaloarylphosphines.

4. A process according to claim 1, wherein the reaction is carried out in an inert solvent selected from the group consisting of halogenated hydrocarbons, nitriles, ketones, esters and mixtures thereof.

5. A process according to claim 1, wherein the reaction is carried out at a temperature of from -10° C. to 100° C.

6. A process according to claim 1, wherein the reaction is carried out in the presence of a halogen compound.

7. A process according to claim 6, wherein the halogen alkaline earth metal halides, quaternary phosphonium halides, iodine halides, bromine halides, quaternary ammonium iodides, quaternary ammonium bromides, alkali metal iodides, alkali metal bromides, phosphorus iodide, phosphorus bromide, alkyl iodides, aralkyl iodides, hydrogen iodide and hydrogen bromide.

8. A process according to claim 6, wherein the halogen compound is used in an amount of 1/1000 2 times as much arylphosphine, in moles.

9. A process for preparing trans-2,2-dimethyl-3(2,2-dihalovinyl)-cyclopropane carboxylic acid halides which comprises reacting a pyridine compound with cis- or a cis/trans-mixture of 2,2-dimethyl-3-(2,2-dihalovinyl)-cyclopropane carboxylic acid halide of the formula $$\begin{array}{c} CH_3 \quad CH_3 \quad O \\ X \quad \diagdown C \diagup \quad \parallel \\ \diagdown C=CH-CH-CH-C-Y \\ X \diagup \end{array}$$

wherein both X and Y are halogen atoms, respectively, in the presence of an iodine compound.

10. A process according to claim 9, wherein the the pyridine compound is used in an amount of 1/100 -5 times as much acid halide, in moles.

11. A process according to claim 9, wherein the pyridine compound is selected from the group consisting of pyridine, picoline, lutidine and isoquinoline.

12. A process according to claim 9, wherein the iodine compound is selected from the group consisting of iodine halides, alkali metal iodides, iodinesubstituted hydrocarbons, quaternary ammonium iodides and quaternary phosphonium iodide.

13. A process according to claim 9, wherein the iodine compound is used in an amount of 1/50 -1 times as much acid halide, in moles.

14. A process according to claim 9, wherein the reaction is carried out in an inert solvent selected from the group consisting of halogenated hydrocarbons, nitriles, ketones, esters and mixtures thereof.

15. A process according to claim 9, wherein the reaction is effected at a temperature of 10-150° C.

16. A process according to claim 1, wherein X is a halogen atom selected from the group consisting of fluorine, chlorine and bromine; and Y is a halogen atom selected from the group consisting of chlorine and bromine.

17. A process according to claim 16, wherein Y is chlorine.

18. A process according to claim 9, wherein X is a halogen atom selected from the group consisting of fluorine, chlorine and bromine; and Y is a halogen atom selected from the group consisting of chlorine and bromine.

19. A process according to claim 18, wherein Y is chlorine.

20. A process according to claim 1, wherein the acid halide is the cis-isomer alone or a cis/trans-mixture rich in the cis-isomer.

21. A process according to claim 9, wherein the acid halide is the cis-isomer alone or a cis/trans-mixture rich in the cis-isomer.

22. A process according to claim 1, wherein the arylphosphine is used in an amount of 1/100-½ times as much acid halide, in moles.

23. A process according to claim 8, wherein the halogen compound is used in an amount of 1/50-½ times as much arylphosphine, in moles.

24. A process according to claim 1, wherein the reaction is carried out at a temperature of from 0-80° C.

25. A process according to claim 1, wherein the reaction is carried out over a time period of from 10 minutes to 20 hours.

26. A process according to claim 9, wherein the pyridine compound is used in an amount of ¼-1 times as much acid halide, in moles.

27. A process according to claim 9, wherein the iodine compound is used in an amount of 1/20-¼ times as much acid halide, in moles.

28. A process according to claim 9, wherein the reaction is effected at a temperature of 60-120° C.

29. A process according to claim 9, wherein the reaction is carried out over a period of time of from 1-15 hours.

* * * * *